(12) United States Patent
Zenhausern

(10) Patent No.: US 9,441,184 B2
(45) Date of Patent: Sep. 13, 2016

(54) FLORAL PERFUMING COMPOSITIONS AS SUBSTITUTES FOR LILIAL®

(71) Applicant: FIRMENICH SA, Geneva (CH)

(72) Inventor: Jean-Michel Zenhausern, Geneva (CH)

(73) Assignee: Firmenich SA, Geneva (CH)

( * ) Notice: Subject to any disclaimer, the term of this patent is extended or adjusted under 35 U.S.C. 154(b) by 230 days.

(21) Appl. No.: 14/348,608

(22) PCT Filed: Sep. 17, 2012

(86) PCT No.: PCT/EP2012/068186
§ 371 (c)(1),
(2) Date: Mar. 30, 2014

(87) PCT Pub. No.: WO2013/045301
PCT Pub. Date: Apr. 4, 2013

(65) Prior Publication Data
US 2014/0234244 A1 Aug. 21, 2014

(30) Foreign Application Priority Data

Sep. 30, 2011 (EP) .................................. 11183426

(51) Int. Cl.
*C11B 9/00* (2006.01)
*A61Q 13/00* (2006.01)
*C11D 3/50* (2006.01)
*A61K 8/33* (2006.01)

(52) U.S. Cl.
CPC .............. *C11B 9/0061* (2013.01); *A61K 8/33* (2013.01); *A61Q 13/00* (2013.01); *C11B 9/0049* (2013.01); *C11D 3/50* (2013.01)

(58) Field of Classification Search
CPC combination set(s) only.
See application file for complete search history.

(56) References Cited

U.S. PATENT DOCUMENTS

| | | | |
|---|---|---|---|
| 6,323,173 B1 | 11/2001 | Winter et al. | |
| 2009/0130043 A1* | 5/2009 | Moretti | C07C 35/36 424/65 |
| 2012/0004328 A1 | 1/2012 | Huchel et al. | |
| 2013/0017990 A1 | 1/2013 | Huchel et al. | |

FOREIGN PATENT DOCUMENTS

| | | |
|---|---|---|
| DE | 10 2009 001570 A1 | 9/2010 |
| WO | WO 2009/027957 A2 | 3/2009 |
| WO | WO 2010/105873 A2 | 9/2010 |
| WO | WO 2010/105874 A1 | 9/2010 |
| WO | WO2012136651 A1 * | 10/2012 |

OTHER PUBLICATIONS

International Search Report and Written Opinion, application No. PCT/EP2012/068186, mailed Dec. 10, 2012.
Vial et al., Helv. Chim. Acta, 88(12):3109-3117 (2005).

* cited by examiner

*Primary Examiner* — Michael G Hartley
*Assistant Examiner* — Robert Cabral
(74) *Attorney, Agent, or Firm* — Winston & Strawn LLP

(57) ABSTRACT

A floral fragrance composition for use as a replacement for 3-(4-tertbutylphenyl)-2-methylpropanal (LILIAL®) that is a primary perfuming ingredient composition that includes a first perfuming ingredient of (2,5-dimethyl-2,3-dihydro-IH-inden-2-yl)methanol (LILYFLORE®) in an amount of 5 to 25% by weight; a second perfuming ingredient of a dimethyl-5-indanyl propanal compound in an amount of 0.2 to 10% by weight; and one or more secondary perfuming ingredients including at least one of 3-methyl-5-phenylpentanal, decanal, octanal, cuminic aldehyde, cuminic alcohol, carvone, tetrahydro-2-isobutyl-4-methyl-4(2H)-pyranol, or cis-7-P-menthanol.

18 Claims, No Drawings

FLORAL PERFUMING COMPOSITIONS AS SUBSTITUTES FOR LILIAL®

BACKGROUND

The present invention relates to the field of perfumery. More particularly, it concerns a fragrant composition which is useful as a replacement for LILIAL® in standard perfuming formulations. LILIAL®, 3-(4-tert-butylphenyl)-2-methylpropanal, is a perfuming ingredient that has been used for imparting a floral note to various perfuming compositions and perfumed articles, but which is more and more limited in use due to increasing toxicological concerns.

As it exists some concerns related to the regulations which are limiting the use of LILIAL® in perfuming application, there is a need for substitutes for that compound. In this regard, WO2010/105874A1 discloses compositions that can be used as a LILIAL® surrogate. While the amount of LILIAL® in the composition is reduced, some still remains in the formulation. Thus, at best, this document teaches how to limit LILIAL® to a lesser amount in such composition but not how to remove or replace it.

WO2010/105873A2 discloses compositions comprising at least two to as many as five or more compounds that could be used to substitute for LILIAL®. Compounds that are mentioned include burgeonal, dimethylphenylethylcarbinol, MAYOL®, mugetanol, citrusal, silvial, cyclamenaldehyde and FLOROL®. The compositions described in this document require the presence of certain compounds such as burgeonal, silvial, and cyclamenaldehyde which are also starting to face raising questions on a toxicologal level. Thus, the document does not present a practical or long term solution to the replacement of LILIAL®.

WO 2009/027957A2 describes a number of different compounds for formulation into "cocktails" for the replacement of p-tert-butyl-alpha-methyldihydrocinnamic aldehyde. A large number of compounds and cocktails are disclosed but a clear composition for replacement of LILIAL® is not.

Thus, there remains a need for a fragrant composition which is useful as a LILIAL® replacement in standard perfuming formulations that provide floral odor characters.

SUMMARY OF THE INVENTION

The fragrance compositions of the present invention now remedy the deficiencies of the prior art by providing a strong and long lasting pleasant floral scent without the use of LILIAL® or other perfuming ingredients which may become limited in the future.

Accordingly, the present invention relates to a floral fragrance composition for use as a replacement for 3-(4-tert-butylphenyl)-2-methylpropanal (LILIAL®), comprising:
- a primary perfuming mixture comprising or consisting of (2,5-dimethyl-2,3-dihydro-1H-inden-2-yl)methanol (LILYFLORE®) in an amount of 5 to 25% by weight, and 3-(gem-dimethyl-5-indanyl)propanal compound in an amount 0.2 to 10% of by weight; and
- one, two, three or more additional secondary perfuming ingredients. The amounts in % by weight are based in each case on the total weight of the fragrance composition.

The present invention also relates to a perfumed consumer article of the perfuming composition disclosed herein and a consumer article, such as a perfume, a fabric care product, a body-care product, an air care product or a home care product.

The invention also relates to a method for providing a floral fragrance composition characterized in that the perfuming ingredient (LILIAL®) of a floral fragrance composition is replaced with a mixture of the first and second perfuming ingredients described herein so that the resulting fragrance composition provides a floral note without the inclusion of LILIAL® or other perfuming ingredients which may become limited in the future.

In addition, the invention relates to the use of a mixture of the first and second perfuming ingredients described herein as a substitute or replacement for LILIAL® in a floral fragrance composition or a floral fragranced consumer article.

DETAILED DESCRIPTION OF THE INVENTION

A floral fragrance composition is now provided for use as a replacement for 3-(4-tert-butylphenyl)-2-methylpropanal (LILIAL®). This composition includes a number of fragrance ingredients which are environmental friendly, at least when used in the amounts disclosed herein and which are not restricted.

The present invention's floral fragrance composition comprises:
- a primary perfumery mixture, as defined below and in the amount as defined below;
- at least one secondary perfuming ingredient, as defined below and in the amount as defined below;
- one or more optional perfuming ingredients, as defined below and in the amount as defined below.

Advantageously, the primary perfumery mixture includes, or consists of, two primary perfuming ingredients. The first primary perfuming ingredient is (2,5-dimethyl-2,3-dihydro-1H-inden-2-yl)methanol compound, the compound known as LILYFLORE® (Firmenich SA). This first perfuming ingredient is present in an amount of 5 to 25% by weight and preferably 10 to 20% by weight. The second primary perfuming ingredient is a 3-(gem-dimethyl-5-indanyl)propanal, also known as HIVERNAL® (Firmenich SA) and it is exactly a mixture of the two isomers 3-(3,3-dimethyl-5-indanyl)propanal and 3-(1,1-dimethyl-5-indanyl)propanal usually in a molar ratio 4/1 to 6/1. This second perfuming ingredient or mixture is typically present in an amount of 0.2 to 10% by weight, and to preferably in an amount of 0.5 to 5% by weight. For the sake of clarity it as to be specified that when an amount is given in % by weight, it means in percentage of the total weight of the inventive composition unless otherwise mentioned. The same is true when the amount is given in ppm by weight.

At least one secondary perfuming ingredient is included in the composition. Any one of a number of secondary perfuming ingredients can be included as desired to achieve the desired nuances of the floral odor character. A skilled perfumist knows how to select such ingredients or combinations thereof to provide different or desirable floral odor character imparting perfuming compositions. A number of different perfuming ingredients and preferred combinations are disclosed herein.

One preferred composition includes at least two secondary perfuming ingredients in combination with the primary perfuming mixture.

One preferred composition includes at least three or four secondary perfuming ingredients in combination with the primary perfuming mixture.

According to an embodiment of the invention, the secondary perfuming ingredients are selected from:
- at least one of 3-methyl-5-phenylpentanal, decanal or octanal in a total amount of 20 ppm to 1000 ppm by weight and preferably 30 ppm to 500 ppm; and/or
- at least one of cuminic aldehyde (4-isopropylbenzaldehyde), cuminic alcohol, or carvone (dextro ((+)-(S)-1 (6),8-P-menthadien-2-one)) in a total amount of 20 ppm to 2000 ppm by weight and preferably 50 ppm to 300 ppm; and/or
- at least one of tetrahydro-2-isobutyl-4-methyl-4(2H)-pyranol (FLOROL®) or cis-7-P-menthanol (MAYOL®) in a total amount of 60% to 95% and preferably 65% or 75% to 90% in weight.

According to any one of the embodiments of the invention, the floral fragrance composition includes at least three secondary perfuming ingredients selected from the previously disclosed groups. According to any one of the embodiments of the invention, the composition includes at least three secondary perfuming ingredients and at least one which is selected from each of the previously disclosed groups of secondary perfuming ingredients.

According to any one of the embodiments of the invention, the invention's floral fragrance composition optionally includes one or more optional perfuming ingredients selected from Citronellal, (+)-(4R)-1-P-menthene-9-carbaldehyde, lemongrass oil, (E) or (Z) 4-decenal, or (E) or (Z) 3-dodecenal, in a total amount of 0 ppm to 1500 ppm by weight.

According to any one of the embodiments of the invention, other optional perfuming ingredients can be selected amongst

| Chemical name | Trivial/Trade Name |
|---|---|
| n-Pentyl salicylate | Amyl Salicylate |
| phenylmethyl 2-hydroxy-benzoate | Benzyl Salicylate |
| (Z)-3-hexenyl 2-hydroxy-benzoate | Cis-3-hexenyl Salicylate |
| cyclohexyl 2-hydroxy-benzoate | Cyclohexyl Salicylate |
| 4-(tricyclo[5.2.1.0(2,6)]decan-8-ylidene)butanal | Dupical ® |
| 4,8-Dimethyldeca-4,9-dienal | Floral Super ® |
| 3-(3-isopropyl-1-phenyl)butanal | Florhydral ® |
| hexyl 2-hydroxy-benzoate | Hexyl Salicylate |
| 3-(1,3-benzodioxol-5-yl)-2-methylpropanal | Helional |
| 2,6-Dimethyl-5-heptenal | Melonal |
| 2,6,10-Trimethy1-9-undecenal | Adoxal |
| 7-propyl-2H,4H-1,5-benzodioxepin-3-one | Aldolone ® | in a total amount of 0 ppm to 1000 ppm by weight.

When the odor of the inventive floral fragrance compositions are compared with that of the prior art LILIAL® substitute compositions, the present floral fragrance compositions distinguish themselves by a stronger and more pleasant floral note that is longer lasting that prior art LILIAL® substitute containing compositions. Furthermore, the present invention's floral fragrance compositions, when compared to other known substitutes of LILIAL®, are the ones which do have an overall odor and performance to profile much closer to the one of LILIAL®.

This is quite surprising since as disclosed in the prior art (see U.S. Pat. No. 6,323,173 or Vial et al. in *Helv. Chem. Comm*, 2005, 3109) both the primary perfuming ingredients, which are the ones imparting the main olfactive character and the performance, have odor profiles with significant difference, e.g. LILYFLORE® has hydroxycitronellal and humic notes not present in Lilial® and HIVERNAL® has a lily of the valley note. Surprisingly, we have found that in the present invention the two compounds have a synergistic effect wherein the undesired notes of the two separate compounds are not perceivable and the overall effect is of the LILIAL® type.

As mentioned above, the present invention's floral perfuming composition can be used as a replacement for 3-(4-tert-butylphenyl)-2-methylpropanal (LILIAL®), i.e. can be used as perfuming ingredient in the composition of a perfume composition.

Therefore, another object of the present invention is a perfuming composition comprising:
i) as perfuming ingredient, one invention's floral fragrance composition as defined above;
ii) at least one ingredient selected from the group consisting of a perfumery carrier and a perfumery base; and
iii) optionally at least one perfumery adjuvant.

"Perfumery carrier" means a material which is practically neutral from a perfumery point of view, i.e., that does not significantly alter the organoleptic properties of perfuming ingredients. This carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

"Perfumery base" means a composition comprising at least one perfuming co-ingredient. Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Furthermore, the invention's composition can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one invention composition, as defined above; and
ii) a perfumery consumer base;
is also an object of the present invention.

For the sake of clarity, it has to be mentioned that, by "consumer article" it is meant a product which is expected to deliver at least a perfuming effect, in other words it is a perfumed consumer article. For the sake of clarity, optionally additional benefit agents, corresponding to a consumer product which is compatible with perfuming ingredients and is expected to deliver a pleasant odor to the surface to which it is applied (e.g. skin, hair, textile, or home surface). In other words, a perfumed consumer article according to the invention comprises the functional formulation, as well as optionally additional benefit agents, corresponding to the desired consumer product, e.g., a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable consumer articles can be a perfume, such as a fine perfume, a cologne or an after-shave lotion; a fabric care product, such as a liquid or solid detergent, a fabric softener, a fabric refresher, an ironing water, a paper, or a bleach; to a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's composition, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the floral composition according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are as previously noted on the order of 0.1% to 5% by weight, or even more, of the floral composition of the invention based on the weight of the composition into which they are incorporated. Lower concentrations, such as on the order of 0.01% to 1% by weight, can be used when these floral compositions are incorporated into perfumed articles, percentage being relative to the weight of the article.

EXAMPLES

The invention will now be described in further detail by way of the following examples, which illustrate preferred embodiments of the invention.

Example 1

Preparation of a Perfuming Composition According the Invention

A perfuming composition according to the invention (CP-IN-1) was prepared by admixing the following ingredients:

| Parts by weight | Ingredient |
| --- | --- |
| 6 | 0.1%* Cuminic aldehyde |
| 4 | 0.1%* Citronellal |
| 28 | Dipropylene glycol |
| 40 | FLOROL ® [1] |
| 4 | 10%* HIVERNAL ® [2] |
| 8 | LILYFLORE ® [3] |
| 4 | 0.1%* 3-Methyl-5-phenylpentanal |
| 6 | 0.01%* (E)-4-decenal |
| 100 | |

*in dipropylene glycol
[1] tetrahydro-2-isobutyl-4-methyl-4(2H)-pyranol; origin: Firmenich SA, Geneva, Switzerland
[2] mixture of 3-(3,3-dimethyl-5-indanyl)propanal and 3-(1,1-dimethyl-5-indanyl)propanal; origin: Firmenich SA, Geneva, Switzerland
[3] (2,5-dimethyl-2,3-dihydro-1H-inden-2-yl)methanol; origin: Firmenich SA, Geneva, Switzerland A comparative perfuming composition (CP-OUT-1) was prepared by admixing the following ingredients:

| Parts by weight | Ingredient |
| --- | --- |
| 6 | 0.1%* Cuminic aldehyde |
| 4 | 0.1%* Citronellal |
| 40 | FLOROL ® [1] |
| 36 | Dipropylene glycol |
| 4 | 10%* HIVERNAL ® [2] |
| 4 | 0.1%* 3-Methyl-5-phenylpentanal |
| 6 | 0.01%* (E)-4-decenal |
| 100 | |

*in dipropyleneglycol
[1] tetrahydro-2-isobutyl-4-methyl-4(2H)-pyranol; origin: Firmenich SA, Geneva, Switzerland
[2] mixture of 3-(3,3-dimethyl-5-indanyl)propanal and 3-(1,1-dimethyl-5-indanyl)propanal; origin: Firmenich SA, Geneva, Switzerland As noted, CP-OUT-1 does not contain LILYFLORE® and is representative of a prior art formulation.

A comparative perfuming composition (CP-OUT-2) was prepared by admixing the same ingredients as (CP-IN-1) but replacing HIVERNAL® Dipropylene glycol.

A comparative perfuming composition (CP-OUT-3) was prepared by admixing the following ingredients:

| Parts by weight | Ingredient |
| --- | --- |
| 88 | Dipropylene glycol |
| 4 | 10%* HIVERNAL ® |
| 8 | LILYFLORE ® |
| 100 | |

As noted, CP-OUT-3 does not contain the secondary perfumery ingredients.

Example 2

Preparation of a Perfuming Composition

A perfuming composition for a Fabric Softener (CFS) was prepared by admixing the following ingredients:

| Parts by weight | Ingredient |
| --- | --- |
| 20 | Benzyl acetate |
| 20 | 1,1-Dimethyl-2-phenylethyl acetate |
| 10 | Styrallyl acetate |
| 100 | Hexylcinnamic aldehyde |
| 1 | AMBRETTOLIDE ® [1] |
| 50 | 1,4-Dioxa-5,17-cycloheptadecanedione |
| 1 | 10%* Gamma undecalactone |
| 1 | 10%* 4-(4-Hydroxy-1-phenyl)-2-butanone |
| 30 | 10%* CETALOX ® [2] |
| 20 | Citronellal |
| 20 | CORANOL ™ [3] |
| 2 | (1'R,E)-2-ethyl-4-(2',2',3'-trimethyl-3'-cyclopenten-1'-yl)-2-buten-1-ol |
| 5 | 1%* 1-(2,6,6-trimethyl-1-cyclohexen-1-yl)-2-buten-1-one |
| 20 | 50%* elemi oil |
| 25 | EXALTOLIDE ® [4] |
| 100 | HABANOLIDE ® [5] |
| 40 | 3-(1,3-benzodioxol-5-yl)-2-methylpropanal |
| 3 | 10%* Indol |
| 20 | ISO E ® SUPER [6] |
| 20 | Alpha iso methylionone |
| 50 | Linalol |
| 3 | 10%* Crystal moss |
| 5 | MUSCENONE ® DELTA [7] |
| 200 | HEDIONE ® [8] |
| 5 | 10%* NEOBUTENONE ® [9] |
| 5 | 10%* NIRVANOL ® [10] |
| 125 | Phenethylol |
| 25 | Phenylhexanol |
| 3 | 10%* 9-Decen-1-ol |
| 30 | 2,2,2-trichloro-1-phenylethyl acetate |
| 20 | Cyclohexyl salicylate |
| 15 | 10%* Vanilline |
| 3 | 10%** 1,3-Undecadien-5-yne |
| 3 | 2,4-Dimethyl-3-cyclohexene-1-carbaldehyde |
| 1000 | |

*in dipropyleneglycol
**in isopropyle myristate
[1] 16-hexadecanolide; origin: Firmenich SA, Geneva, Switzerland
[2] dodecahydro-3a,6,6,9a-tetramethyl-naphtho[2,1-b]furan; origin: Firmenich SA, Geneva, Switzerland
[3] 4-cyclohexyl-2-methyl-2-butanol; origin: Firmenich SA, Geneva, Switzerland
[4] pentadecanolide; origin: Firmenich SA, Geneva, Switzerland
[5] pentadecenolide; origin: Firmenich SA, Geneva, Switzerland
[6] 1-(octahydro-2,3,8,8-tetramethyl-2-naphthalenyl)-1-ethanone; origin: International Flavors & Fragrances, USA
[7] 3-methyl-5-cyclopentadecen-1-one; origin: Firmenich SA, Geneva, Switzerland
[8] methyl dihydrojasmonate; origin: Firmenich SA, Geneva, Switzerland
[9] 1-(5,5-dimethyl-1-cyclohexen-1-yl)-4-penten-1-one; origin: Firmenich SA, Geneva, Switzerland
[10] 3,3-dimethyl-5-(2,2,3-trimethyl-3-cyclopenten-1-yl)-4-penten-2-ol; origin: Firmenich SA, Geneva, Switzerland 100 parts by weight of LILIAL® (3-(4-tert-butylphenyl)-2-methylpropanal) was added to the CFS composition to obtain CFS-LIL.

100 parts by weight of CP-IN-1 according to Example 1 was added to another CFS composition to obtain CFS-(CP-IN-1).

100 parts by weight of CP-OUT-1 according to comparative Example 1 was added to another CFS composition to obtain CFS-(CP-OUT-1).

100 parts by weight of CP-OUT-2 according to comparative Example 1 was added to another CFS composition to obtain CFS-(CP-OUT-2).

100 parts by weight of CP-OUT-3 according to comparative Example 1 was added to another CFS composition to obtain CFS-(CP-OUT-3).

Each new composition was then incorporated into a standard un-perfumed fabric softener base which was used in the washing of standard cotton tissues to perfume those tissues with one of the CFS-LIL, CFS-(CP-IN-1), CFS-(CP-OUT-1), CFS-(CP-OUT-2) and CFS-(CP-OUT-3) compositions. These tissues were then evaluated olfactively at different times by a panel of perfumers for both odor strength (performance) and pleasantness.

On an evaluation of the wet tissues just after washing, CFS-LIL was judged as the strongest odor strength while CFS-(CP-IN-1) and CFS-(CP-OUT-1) where equally preferred in terms of pleasantness; CFS-(CP-OUT-2) was judged being weaker and less elegant and CFS-(CP-OUT-3) was judged being less pleasant than CFS-(CP-IN-1). After 24 hours of air dry, the first three samples (the best ones) were again rated in terms of odor strength and CFS-(CP-IN-1) was more higher rated in terms of pleasantness. After 72 hours of air dry, the CFS-LIL and CFS-(CP-IN-1) samples were unanimously rated as very close in terms of strength (performance) and pleasantness, while CFS-(CP-OUT-1) was clearly behind in particular in terms of strength (performance). This to demonstrates the unexpected advantages based on the inclusion of LILIFLORE® in the composition, as it provides similar properties to the composition that contains the now objectionable LILIAL®.

Example 3

Preparation of a Perfuming Composition

A Fine Fragrance Perfume (FFP) was prepared by admixing the following ingredients:

| Parts by weight | Ingredient |
| --- | --- |
| 10 | Isoeugenyl acetate |
| 5 | Citronellyl acetate |
| 35 | Linalyl acetate |
| 10 | 10%* AMBROX® [1] |
| 10 | Methyl anthranilate |
| 10 | 1,4-Dioxa-5,17-cycloheptadecanedione |
| 1 | Gamma undecalactone |
| 5 | 10%* 4-Nonanolide |
| 5 | 10%* decal |
| 6 | dipropylene glycol |
| 80 | ethyl linalol |
| 5 | 10%* Orange flower essential oil |
| 50 | FLOROL® [2] |
| 40 | HABANOLIDE® [3] |
| 230 | HEDIONE® HC [4] |
| 30 | 3-(1,3-benzodioxol-5-yl)-2-methylpropanal |
| 20 | ISO E® SUPER [5] |
| 1 | 3-Hexenyl-methyl carbonate |
| 40 | linalol |
| 15 | MUSCENONE® DELTA [6] |
| 120 | PARADISONE® [7] |
| 20 | Phenethylol |
| 1 | (Z)-3-hexen-1-ol |
| 2 | SANDELA® [8] |
| 4 | santal oil |
| 3 | 10%* (2,2-Dimethoxyethyl)benzene |
| 2 | ylang ylang |
| 5 | CASSIS BASE® [9] |
| 5 | Neroli bigarade essential oil |
| 770 | |

*in dipropyleneglycol
[1] (−)-(8R)-8,12-epoxy-13,14,15,16-tetranorlabdane; origin: Firmenich SA, Geneva, Switzerland
[2] tetrahydro-2-isobutyl-4-methyl-4(2H)-pyranol; origin: Firmenich SA, Geneva, Switzerland
[3] pentadecenolide; origin: Firmenich SA, Geneva, Switzerland
[4] methyl cis-dihydrojasmonate; origin: Firmenich SA, Geneva, Switzerland
[5] 1-(octahydro-2,3,8,8-tetramethyl-2-naphthalenyl)-1-ethanone; origin: International Flavors & Fragrances, USA
[6] 3-methyl-5-cyclopentadecen-1-one; origin: Firmenich SA, Geneva, Switzerland
[7] (+)-methyl cis-dihydrojasmonate; origin: Firmenich SA, Geneva, Switzerland
[8] 5-(2,2,3-trimethyl-3-cyclopentenyl)-3-methylpentan-2-ol; origin: Givaudan SA, Vernier, Switzerland
[9] compounded perfumery base; origin: Firmenich SA, Geneva, Switzerland 100 parts by weight of LILIAL® (3-(4-tert-butylphenyl)-2-methylpropanal) was added to a FFP composition to obtain FFP-LIL.

100 parts by weight of the CP-IN-1 composition was added to another FFP composition to obtain FFP-(CP-IN-1).

100 parts by weight of the CP-OUT-1 composition was added to another FFP composition to obtain FFP-(CP-OUT-1).

Each of the FFP-LIL, FFP-(CP-IN-1) and FFP-(CP-OUT-1) where evaluated olfactively at different times by a panel of perfumers for both odor strength (performance) and pleasantness.

Half hour after admiture, FFP-(CP-IN-1) was preferred in terms of pleasantness.

After 24 hours on a blotter, FFP-LIL was rated marginally stronger than FFP-(CP-IN-1) and FFP-(CP-OUT-1), while FFP-(CP-IN-1) was rated marginally more pleasant.

After 72 hours, again on a blotter, FFP-LIL and FFP-(CP-IN-1) were unanimously rated as very close in terms of strength (performance) and pleasantness, while FFP-(CP-OUT-1) was clearly behind in particular in terms of strength (performance). This again demonstrates the unexpected advantages based on the inclusion of LILIFLORE® in the composition.

What is claimed is:

1. A floral fragrance composition comprising:
    a primary perfumery mixture that includes as first primary perfuming ingredient (2,5-dimethyl-2,3-dihydro-1H-inden-2-yl) methanol in an amount of 5 to 25% by weight and as second primary perfuming ingredient 3-(gem-dimethyl-5-indanyl)propanal in an amount of 0.2 to 10% by weight ; and
    at least one secondary perfuming ingredient selected amongst
        at least one of 3-methyl-5-phenylpentanal, decanal or octanal in a total amount of 20 ppm to 1000 ppm by weight; and/or
        at least one of cuminic aldehyde, cuminic alcohol, or carvone in a total amount of 20 ppm to 2000 ppm by weight; and/or
        at least one of tetrahydro-2-isobutyL-4-methyl-4(2H)-pyranol or cis-7-P-menthanol in a total amount of 60% to 95% by weight;
    wherein the amounts in % by weight and the ppm by weight are based in each case on the total weight of the fragrance composition.

2. A composition according to claim 1, wherein the first primary perfuming ingredient is present in an amount of 10 to 20% by weight and the second primary perfuming ingredient is present in an amount of 0.5 to 5% by weight.

3. A composition according to claim 1, wherein said 3-(gem-dimethyl-5-indanyl)propanal is a mixture of the two isomers 3-(3,3-dimethyl-5-indanyl)propanal and 3-(1,1-dimethyl-5-indanyl)propanal usually in a molar ratio 4/1 to 6/1.

4. A composition according to claim 1, wherein said composition comprises at least two secondary perfuming ingredients.

5. A composition according to claim 1, wherein said composition comprises at least three secondary perfuming ingredients and at least one which is selected from each of the three groups of secondary perfuming ingredients.

6. A composition according to claim 1, wherein said composition further comprises one or more optional perfuming ingredients selected amongst:
    Citronellal, (+)-(4R)-1-P-menthene-9-carbaldehyde, lemongrass oil, (E) or (Z) 4-decenal, or (E) or (Z) 3-dodecenal, in a total amount of 0 ppm to 1500 ppm by weight; and or
    n-pentyl salicylate, phenylmethyl 2-hydroxy-benzoate, (Z)-3-hexenyl 2-hydroxy-benzoate, cyclohexyl 2-hydroxy-benzoate, 4-(tricyclo[5.2.1.0(2,6)]decan-8-ylidene)butanal, 4,8-dimethyldeca-4,9-dienal, 3-(3-isopropyl-1-phenyl)butanal, hexyl 2-hydroxy-benzoate, 3-(1,3-benzodioxol-5-yl)-2-methylpropanal, 2,6-dimethyl-5-heptenal, 2,6,10-trimethyl-9-undecenal, 7-propyl-2H,4H-1,5-benzodioxepin-3-one, in a total amount of 0 ppm to 1000 ppm by weight.

7. A perfuming composition comprising
    i) one floral fragrance composition, as defined in claim 1;
    ii) at least one ingredient selected from the group consisting of a perfumery carrier and a perfumery base; and
    iii) optionally at least one perfumery adjuvant.

8. A perfuming composition, comprising
    i) one floral fragrance composition, as defined in claim 1; and
    ii) a perfumery carrier.

9. A perfuming consumer product comprising:
i) a composition, as defined in claim 1; and
ii) a perfumery consumer base.

10. A perfuming consumer product according to claim 9, characterized in that the perfumery consumer base is a perfume, a fabric care product, a body-care product, an air care product or a home care product.

11. A perfuming consumer product according to claim 9, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

12. A floral fragrance composition comprising:
two primary perfuming ingredients, one of which is (2,5-dimethyl-2,3-dihydro-1H-inden-2-yl)methanol compound in an amount of 5 to 25% by weight and the other of which is a mixture of 3-(3,3-dimethyl-5-indanyl)propanal and 3-(1,1-dimethyl-5-indanyl)propanal in a molar ratio 4/1 to 6/1 and in an amount of 0.2 to 10% by weight; and
at least one secondary perfuming ingredient which is:
at least one of 3-methyl-5-phenylpentanal, decanal or octanal in a total amount of 20 ppm to 1000 ppm by weight;
at least one of cuminic aldehyde (4-isopropylbenzaldehyde), cuminic alcohol, or carvone (dextro ((+)-(S)-1(6),8-P-menthadien-2-one)) in a total amount of 20 ppm to 2000 ppm by weight; or
at least one of tetrahydro-2-isobutyL-4-methyl-4(2H)-pyranol (FLOROL®) or cis-7-P-menthanol (MAYOL®) in a total amount of 60% to 95% by weight;
wherein the amounts are based in each case on the total weight of the fragrance composition.

13. The fragrance composition of claim 12, wherein the 2,5-dimethyl-2,3-dihydro-1H-inden-2-yllmethanol compound is present in an amount of 10 to 20% by weight, the mixture of 3-(3,3-dimethyl-5-indanyl)propanal and 3-(1,1-dimethyl-5-indanyl)propanal is present in amount of 0.5 to 5% by weight, and the secondary perfuming ingredient is:
at least one of 3-methyl-5-phenylpentanal, decanal or octanal in a total amount of 30 ppm to 500 ppm;
at least one of cuminic aldehyde (4-isopropylbenzaldehyde), cuminic alcohol, or carvone (dextro ((+)-(S)-1(6),8-P-menthadien-2-one)) in a total amount of 50 ppm to 300 ppm; or
at least one of tetrahydro-2-isobutyL-4-methyl-4(2H)-pyranol (FLOROL®) or cis-7-P-menthanol (MAYOL®) in a total amount of 75% to 90% by weight.

14. A perfuming composition comprising
i) one floral fragrance composition, as defined in claim 12;
ii) at least one ingredient selected from the group consisting of a perfumery carrier and a perfumery base; and
iii) optionally at least one perfumery adjuvant.

15. A perfuming composition comprising
i) one floral fragrance composition, as defined in claim 12; and
ii) a perfumery carrier.

16. A perfuming consumer product comprising:
i) a composition, as defined in claim 12; and
ii) a perfumery consumer base.

17. A perfuming consumer product according to claim 16, characterized in that the perfumery consumer base is a perfume, a fabric care product, a body-care product, an air care product or a home care product.

18. A perfuming consumer product according to claim 16, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *

UNITED STATES PATENT AND TRADEMARK OFFICE
CERTIFICATE OF CORRECTION

PATENT NO.        : 9,441,184 B2
APPLICATION NO.   : 14/348608
DATED             : September 13, 2016
INVENTOR(S)       : Zanhausern Page 1 of 1

It is certified that error appears in the above-identified patent and that said Letters Patent is hereby corrected as shown below:

In the claims,

Column 10:
Line 20 (claim 1, line 16), after "at least one of tetrahydro-2-", delete "isobutyL" and insert
-- isobutyl --.

Column 11:
Line 34 (claim 12, line 17), after "at least one of tetrahydro-2-", delete "isobutyL" and insert
-- isobutyl --.
Line 41 (claim 13, line 2), after "2,5-dimethyl-2,3-dihydro-1H-inden-2-", delete "yllmethanol" and
insert -- yl)methanol --.

Column 12:
Line 10 (claim 13, line 13), after "at least one of tetrahydro-2-", delete "isobutyL" and insert
-- isobutyl --.

Signed and Sealed this
Twenty-fifth Day of October, 2016

Michelle K. Lee
*Director of the United States Patent and Trademark Office*